United States Patent [19]

Peterson et al.

[11] Patent Number: 5,506,130
[45] Date of Patent: Apr. 9, 1996

[54] MULTIPLE STAGE AFFINITY PROCESS FOR ISOLATION OF SPECIFIC CELLS FROM A CELL MIXTURE

[75] Inventors: Dale R. Peterson; Lynn A. Arlauskas, both of Wilmington, Del.

[73] Assignee: CellPro, Inc., Bothell, Wash.

[21] Appl. No.: 414,045

[22] Filed: Mar. 30, 1995

Related U.S. Application Data

[63] Continuation of Ser. No. 231,586, Apr. 20, 1994, abandoned, which is a continuation of Ser. No. 94,397, Jul. 19, 1993, abandoned, which is a continuation of Ser. No. 759,838, Sep. 13, 1991, abandoned, which is a continuation of Ser. No. 653,466, Feb. 8, 1991, abandoned, which is a continuation of Ser. No. 140,672, Jan. 4, 1988, abandoned.

[51] Int. Cl.$^6$ .................. C12N 5/00; G01N 33/554; G01N 33/553; G01N 33/567
[52] U.S. Cl. .................. 435/240.1; 435/240.241; 435/240.243; 435/7.21; 436/519; 436/526; 436/824
[58] Field of Search .................. 435/240.243, 240.241, 435/240.1, 176, 177, 7.21; 436/824, 526, 519; 530/810

[56] References Cited

U.S. PATENT DOCUMENTS

| | | |
|---|---|---|
| 3,843,324 | 10/1974 | Edelman et al. . |
| 3,947,352 | 3/1976 | Cuatrecasas .................. 210/31 |
| 3,970,518 | 7/1976 | Giaever .................. 435/239 |
| 4,230,685 | 10/1980 | Senyei et al. .................. 436/526 |
| 4,416,777 | 11/1983 | Kuroda et al. .................. 210/446 |
| 4,452,773 | 6/1984 | Molday .................. 424/1.1 |
| 4,619,904 | 10/1986 | Giaever et al. .................. 436/518 |
| 4,710,472 | 12/1987 | Saur .................. 435/287 |

FOREIGN PATENT DOCUMENTS

WO87/04628  8/1987  WIPO .

OTHER PUBLICATIONS

Berenson, et. al. "Positive Selection of Viable Cell Populations Using Avidin–Biotin Immunoadsorption". J. Immunol. Methods, vol. 91, pp. 11–19 1986.
Gaudernack, et. al. "Isolation of Pure Functionally Active CD8$^+$ T Cells" J. Immunol. Methods, vol. 90, pp. 179–187 1986.
Wysocki, et. al. "Panning for Lymphocytes: A Method for Cell Selection" Proc. Natl. Acad. Sciences USA, vol. 75, pp. 2844–2848 1978.
Schleicher, Multisurface Stacked Plate Propagators, in Kruse, et. al. (Eds) *Tissue Culture,* pp. 334–338, Academic Press, New York 1973.
Julius et al., *Proc. Nat. Acad. Sci. USA* 69: 1934–1938, 1972.
Fong, *Cell Separation: Methods and Selected Applications* 2: 203–219, 1983.
Basch et al., *J. Immunol. Methods* 56: 269–280, 1983.
Edelman et al., *Fractionation and Manipulation of Cells* 195–225.
Kumar et al., *Pathology* 16: 53–62, 1984.
Lakow et al., *J. Immunol. Methods* 44: 135–151, 1981.

Rutishauser et al., *Proc. Nat. Acad. Sci. USA* 70: 3894–3898, 1973.

Wigzell et al., *Cell Separation on Antigen–Coated Columns* 23–36, Department of Tumor Biology, Karolinska Institutet, Stockholm 60, Sweden.

Wormmeester et al., *J. Immunol. Methods* 67: 389–394, 1984.

Dangl & Herzenberg, "Selection of Hybridomas and Hybridoma Variants Using the Fluorescence Activated Cell Sorter," *J. Imm. Methods* 52:1–14, 1982.

Juckett & Hultquist, "Chromatography of Erythroblasts on Immobilized Transferrin", *Proc. Soc. for Exp. Biology & Medicine* 172:79–83, 1983.

Fong, "Solid–Phase Fractionation of Lymphoid Cells on Ligand–Coated Plastic Plates," *Cell Separation: Methods & Selected Applications* 2:203–219, 1983.

D. A. Hammer et al., "Affinity Chromatography for Cell Separation: Mathematical Model and Experimental Analysis," *Biotechnology Progress* 3(3):189–204, 1987.

D. C. Torney et al., "Thermodynamics of Cell Adhesion II. Freely Mobile Repellers," *Biophys. J.* 49:501–507, 1986.

C. M. Hertz, et al., "Use of Cell Affinity Chromatography for Separation of Lymphocyte Subpopulations," *Biotechnology and Bioengineering* XXVII:603–612, 1985.

P. Bongrand et al., "Cell–Cell Adhesion: Parameters and Possible Mechanisms," in *Cell Surface Dynamics: Concepts and Models,* A. Perelson, C. DeLisi, and F. Wiegel, eds., Marcel Dekker, Inc., New York, 1984.

H. Wigzell et al., Cell Separation on Antigen–Coated Columns, 1969, J. Exp. Med. 129:23.

J. G. Treleaven et al., Removal of Neuroblastoma Cells from Bone Bone Marrow with Monoclonal Antibodies Conjugated to Magnetic Microspheres, 1984, Lancet 1:70–73.

R. J. Berenson et al., J. Immunol. Methods, 1986 91:179–187.

G. I. Bell et al., Biophys. J. 45 (1984).

Grinnell, Intl. Rev. Cytology, 53:65–144 (1978).

*Primary Examiner*—Marian C. Knode
*Assistant Examiner*—Susan M. Dadio
*Attorney, Agent, or Firm*—Seed & Berry

[57] ABSTRACT

Desired cells are positively separated from a mixture of cells using multiple stages of affinity surfaces. Bound cells from each surface are removed and subjected to a further surface for further enrichment.

11 Claims, 3 Drawing Sheets

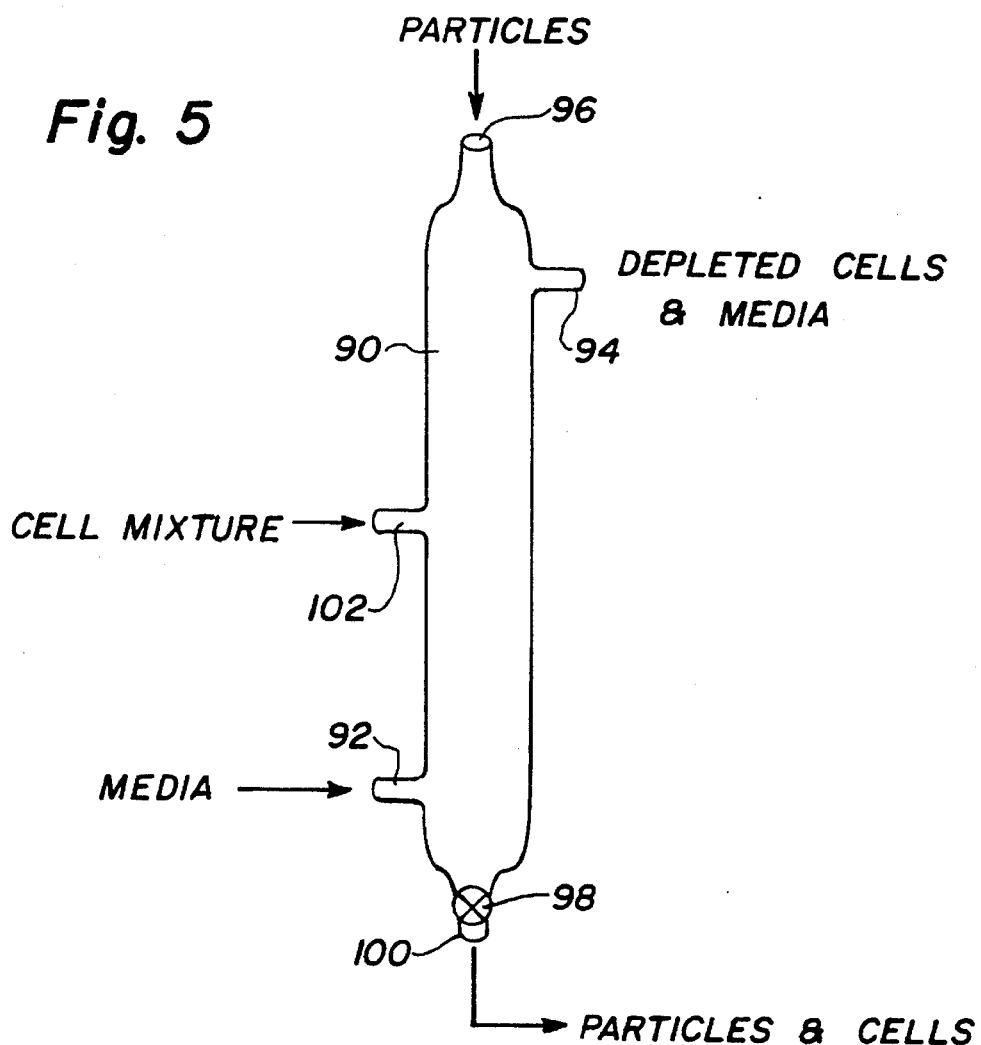
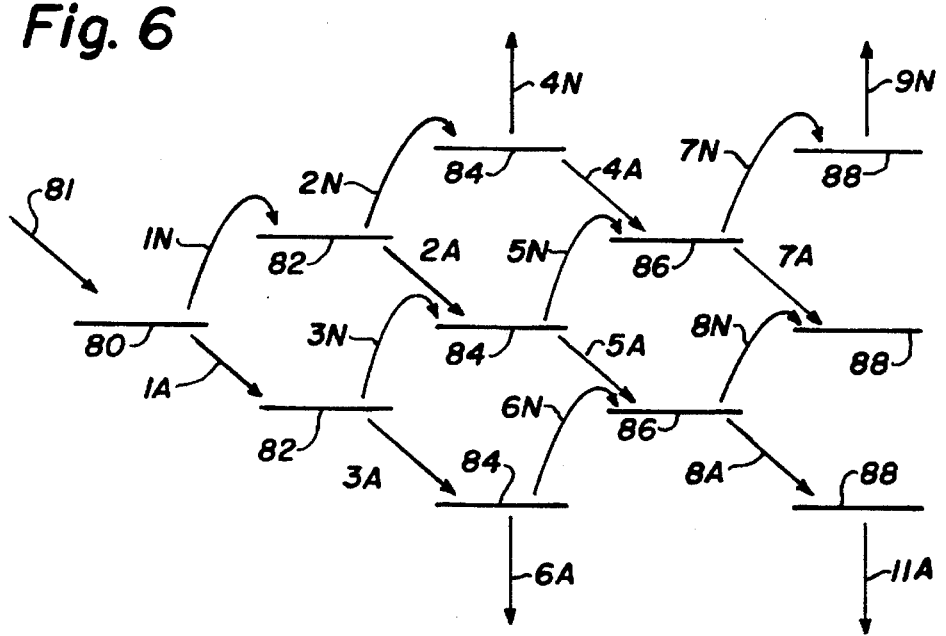

MULTIPLE STAGE AFFINITY PROCESS FOR ISOLATION OF SPECIFIC CELLS FROM A CELL MIXTURE

CROSS-REFERENCE TO RELATED APPLICATION

This application is a continuation of U.S. patent application Ser. No. 08/231,586, filed Apr. 20, 1994, now abandoned; which was a continuation of U.S. patent application Ser. No. 08/094,397, filed Jul. 19, 1993, now abandoned; which was a continuation of U.S. patent application Ser. No. 07/759,838, filed Sep. 13, 1991, now abandoned; which was a continuation of U.S. patent application Ser. No. 07/653,466, filed Feb. 8, 1991, now abandoned; which was a continuation of U.S. patent application Ser. No. 07/140,672, filed Jan. 4, 1988, now abandoned.

FIELD OF THE INVENTION

The invention relates to a multistage, positive selection process for separating specific biological cells from a cell mixture. Positive selection is achieved by contacting the cells with an affinity surface having a high affinity for the cell population to be purified.

BACKGROUND OF THE INVENTION

Cell separation techniques have important potential application in cancer therapies, autoimmune disease therapies, and improved diagnostics. For example, cell affinity devices can be used in extracorporeal therapies that may involve the selective isolation, augmentation, and reintroduction to the host of a specific subset population of cells.

Affinity separation of cells refers to process techniques where a particular subset of a population of cells are bound to support surfaces by means of ligands with specific affinity to molecules or structures on the cell membrane. Cells which lack the membrane molecules or structures are not bound to the support surface and can be removed from the population to effect a separation. Cell affinity techniques have been used widely since Wigzell's description of such a process in 1969 [Wigzell and Anderson (1969) *J. Exp. Med.* 129:23].

Affinity separation processes are commonly used either to deplete cell subpopulations from a mixture or to positively select a specific population from a mixture. The depletion process is much simpler because the bound cells are simply discarded leaving the desired cells behind. Positive selection is much more difficult both because the desired cells are bound to the support and must be removed without damaging them and because a certain proportion of the undesirable cells bind nonspecifically to the affinity surface and contaminate the desired collected cells.

Affinity cell depletion techniques have found some important applications. Researchers prepare specific cell subpopulations for study by systematically depleting a mixture of various subpopulations of cells. For example, Treleavan et al. (Treleavan et al., 1984, *Lancet* 1:70–73) have demonstrated that the concentration of neuroblastoma cells in a bone marrow preparation can be reduced by a factor of about $10^6$ using multiple depletions with antibody-coated magnetic beads.

Two examples of positive selection techniques are those described by Berenson et al. (*J. Immunol. Methods*, 1986, 91:179–187) and Gaudernack et al., *J. Immunol. Methods*, 1986, 91:179–187. Berenson et al. bind biotinylated antibodies to target cells and pass them through a column packed with avidin-coated beads, thereby recovering 64% of a population of human bone marrow cells at a final concentration of 73% when the initial concentration was 7%. Gaudernack et al. use antibody-coated magnetic beads to collect a certain subset of T cells. The initial concentration was 30%, and the positively selected population was 96%; the yield is not mentioned. These purities are not adequate for a large number of attractive applications, such as stem cell transplants, or the preparation of subpopulations for cell biology or immunology studies.

Repeated contacting of cells has been shown to be effective in the depletion of cells from mixtures, but repeated contacting of cells for positive selection of subpopulations has not been reported. This is not surprising since theories of the mechanism of affinity cell binding predict no advantage with multiple stages (Hertz et al., 1985, *Biotech. and Bioeng.*, 27:603–612; Bell et al., 1984, *Biophys. J.* 45; Grinnell, 1978, *Intl. Rev. Cytology*, 53:65–144). There remains a need to be able to recover cells with higher yields and higher purities.

SUMMARY OF THE INVENTION

Contrary to previous theories of affinity separation of cells (Hertz et al., op. cit.; Bell et al., op. cit.; Grinnell, op. cit.), cell binding to immobilized ligands is reversible. The reversible nature of cell binding to immobilized ligands allows the efficient removal and purification of specific subsets of cells from mixtures using multiple stage affinity processes. These processes surpass in efficiency the performance of previously reported processes.

According to this invention, specific biological cells are separated from a cell mixture by a positive selection process which gives both higher cell purity and higher cell recovery than current processes. The invention uses multiple contacting stages. A cell mixture is contacted with a surface having a high affinity for the desired or target cell population. The affinity surface contains immobilized ligand with high affinity for the target cells. Adherent cells are removed from the affinity surface and then reexposed to a second affinity surface with high affinity for the same target cell in a second stage. The number of stages is increased until the required cell purity has been achieved. Cell recovery is increased by reexposing the nonadherent cells from each stage to a fresh affinity surface in each additional stage.

Alternatively, the process may be accomplished using counter-current extraction techniques where nonadherent cells at a given stage are reexposed to the affinity surface of the preceding stage.

BRIEF DESCRIPTION OF DRAWINGS

Further advantages and features of this invention will become apparent from the following description wherein:

FIG. 5 is a schematic representation of a multistage counter-current cell separations system; and FIG. 6 is a schematic representation of a multistage batch type cell separation system.

DETAILED DESCRIPTION OF THE PREFERRED EMBODIMENT

The present invention is an affinity separation process for preparing high purity fractions of cells from mixtures of cells by repeatedly contacting the cells with surfaces coated with immobilized ligands with specific affinity for the desired subpopulation of cells. Cells, as the term is used herein, may include biological cells of any origin, including prokaryotic and eukaryotic organisms. By way of emphasis, noncellular particles including viruses, mycoplasma, and particles in general are included in this definition and can be purified using the affinity separation process of the invention.

Figure 1:
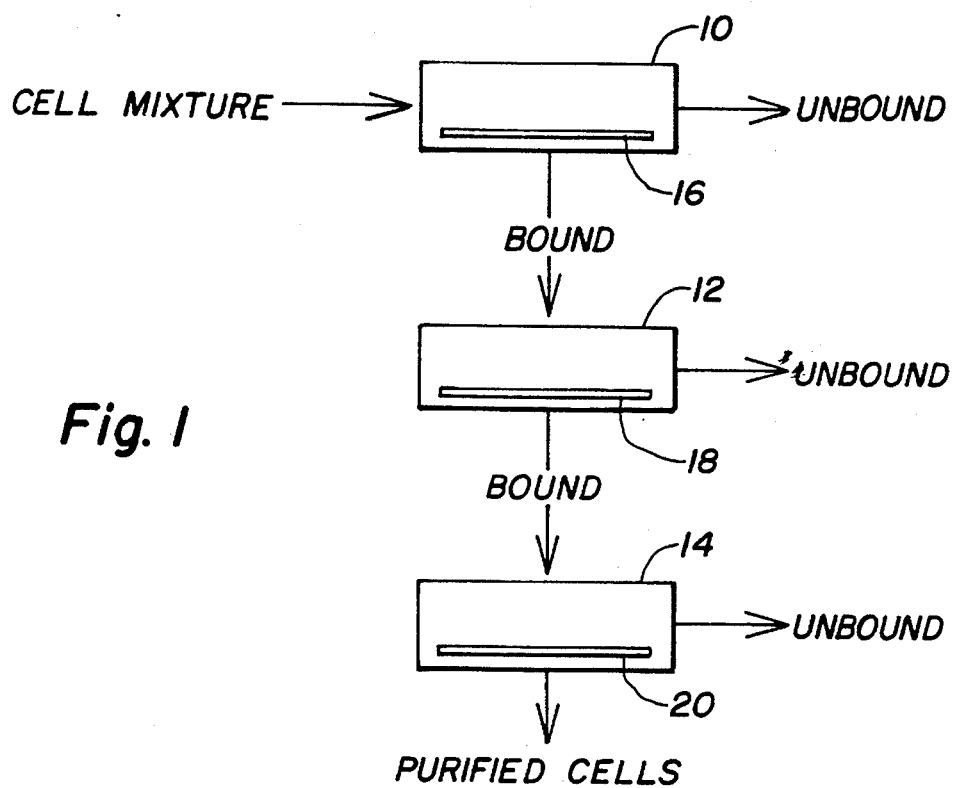
FIG. 1 is a block representation of the multiple stage affinity separation process of this invention for the positive selection of cells.
Figure 2:
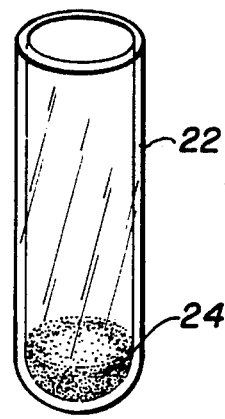
FIG. 2 is a schematic representation of a container with bound ligands which may be used for the stages of FIG. 1.

A multiple stage affinity cell separation process or multiple stage positive cell selection process according to this invention is shown in block diagrammatic form in FIG. 1. Blocks 10, 12, and 14 represent affinity cell separation devices with affinity contact surfaces 16, 18, and 20, respectively. These devices 10, 12, and 14, as is known in the art, may include bead columns, petri dishes, magnetic beads, fiber arrays, porous membranes, hollow fibers, roller bottles, emulsions, slurries, and the like. The surfaces 16, 18, and 20 in the devices may be formed of any of the materials known to be useful for this purpose and include gels (such as Sepharose), polymers (such as polyarylates, polyesters, polyaldehydes, polyimides, polyvinylpyrrolidones, polyaramides, polyacrylonitriles, polysulfones, cellulosics, ionomers, and fluoropolymers), proteins, lipids, surfactants, glasses, and ceramics. The surface of a device, for example, the bottom of a polystyrene container 22, such as illustrated in FIG. 2, is coated with the immobilized ligand 24. The immobilized ligand 24 has affinity for the cell population that is desired to be isolated. The cell separation devices 10, 12, and 14 may each be the same or differ in type and may number two or more for each stage.

The cell contacting surfaces are coated with a ligand 24 which binds cells with a specific affinity. The immobilized ligand may be, for example, an antibody molecule recognizing a specific antigen on the cell surface. The immobilized ligand could also be a specific ligand molecule, such as a lectin, dye, or a receptor ligand, that is bound by a receptor or ligand-binding molecule on the surface of the cell to be purified. The affinity ligand may also be, for example, biotin, avidin, protein A, an enzyme, an enzyme substrate, or a receptor. Sandwiches or combinations of ligands and ligand-binding molecules may be used. For example, T3-bearing cells may be captured by using a mouse monoclonal antibody specific for T3 and an immobilized antibody specific for mouse immunoglobulin, i.e., the mouse anti-T3 antibody. Molecular spacers or bridges may be used to facilitate interaction of the ligand and ligand-binding molecules. The same or different affinity ligands may be used at each step or stage in the multiple stage separation process.

The affinity ligands may be bound to the cell contacting surface by any of the well-known techniques. For example, physical adsorption, covalent chemistry, physical entrapment, hydrophobic interactions, or Van der Waals interactions may be used. Current techniques for the attachment of proteins to solid supports are reviewed in *Affinity Chromatography and Related Techniques,* edited by T. C. J. Gribnau, J. Vissen, and R. J. F. Nivand Elsevier, 1982.

The media may be any suitable media that is not harmful to the cells, the ligand, or the ligand-binding molecule. Commonly used media include Hanks balanced salt solutions, RPMI 1640, phosphate buffered saline, Eagle's or Dulbeco's minimum essential media. Other common media and additives are described in. *American Type Culture Collection* (Rockville, Md.) *Catalogue of Cell Lines and Hybridomas,* 5th edition, 1485, pp. 263–273.

The method of this invention, as depicted in FIG. 1, includes placing a mixture of cells, containing desired cells to be separated, in a first medium such that the cells contact the surface 16 and the desired cells become bound to the ligands thereon. Unfortunately some undesired cells also become attached. The cells which do not become attached to the surface ligands are washed from the surface by additional media and discarded. Cells which are bound or adhere to the affinity surface 16 are removed from the affinity surface. The cells may be removed by any well known method including scraping, agitating, fluid shear, use of an elution buffer, or by natural desorption. These removed cells are resuspended in a fresh medium and introduced in the second device 12.

The mixture of removed cells is contacted with the affinity ligand-containing surface 18 in the second device 12. After contact with the affinity surface, the unbound cells are washed out and the bound cells are removed from the surface 18. The removed cells are resuspended in fresh medium and introduced into a third device 14. After contact with the third device's affinity surface 20, the unbound cells are again washed out and the bound cells are removed to constitute the purified cells. This process of positive selection and elution of the positively selected cells can be repeated as many times as necessary to achieve the desired degree of purity and yield.

In its simplest form, the method of the invention may use petri dishes coated with an appropriate ligand (antibody) recognizing a molecular marker specific for the cell population to be purified. Cell mixtures are allowed to settle to the bottom and bind to the surface of the antibody-coated dish. Nonadherent cells are then washed away. The adherent cells are scraped and the free scraped cells are resuspended in fresh media. The resuspended cells are then poured into a fresh antibody-coated dish, and the procedure repeated until the adherent cells are of the desired purity.

Figure 3:
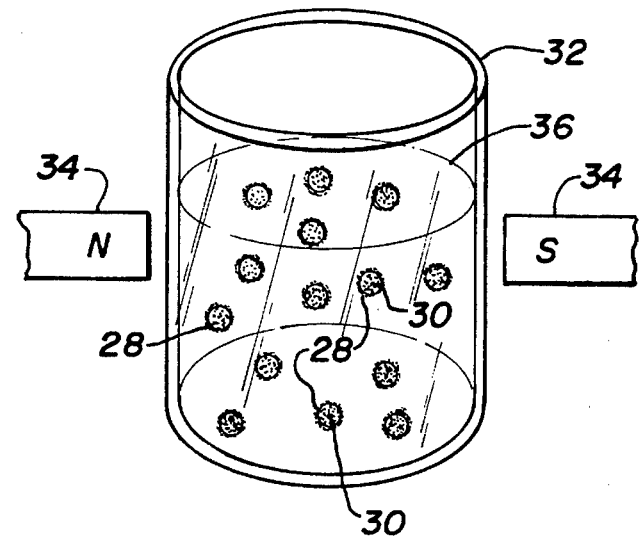
FIG. 3 is a schematic representation of magnetic particles coated with ligands that may provide the surfaces for any of the stages of FIG. 1.

Alternatively, the method of this invention may immobilize ligands 28 on magnetic particles 30, as seen in FIG. 3, in a known manner. The particles are placed in a container 32 in a fluid medium 36 suitable for the ligands and cells to be separated. Magnets 34 are moved into position along the sides of the container after the cells to be separated are mixed with the magnetic particles 30 for binding to the ligands 28 thereon. This secures the particles 30 with the attached desired cells to the side walls of the container 32 so that the unattached cells and medium may be discarded and the secured particles washed thoroughly. The container is again filled with a fresh medium and the magnets withdrawn (or deenergized) to release the particles. The desired cells are allowed to be released from the particles by natural desorption. The released cells are collected and introduced into a second container (not shown except as block 10, FIG. 1) with a fresh medium and ligand-coated magnetic particles. The procedure described above is repeated to further increase the purity of the cells.

Figure 4:
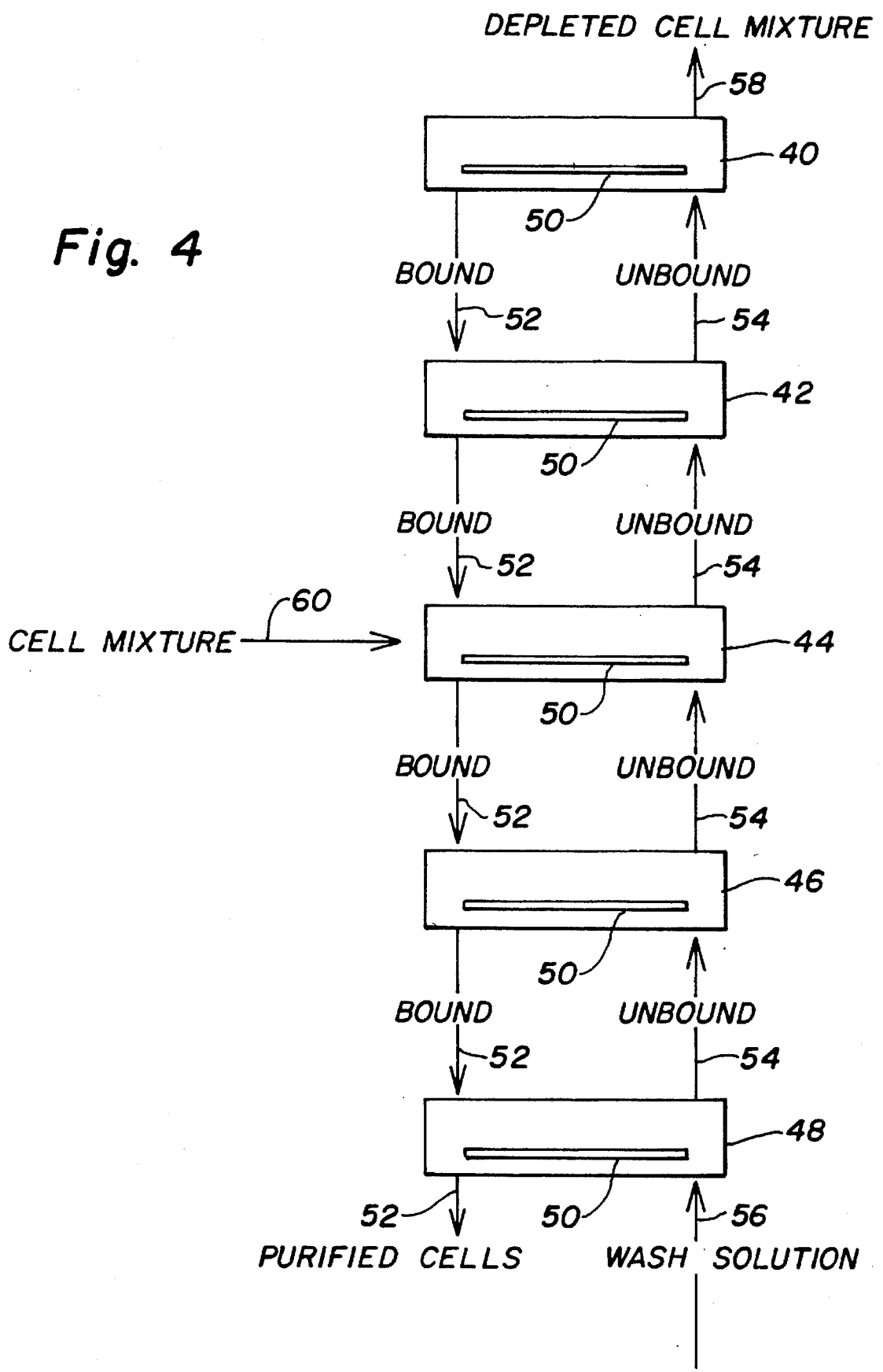
FIG. 4 is a block representation of a counter-current affinity cell fractionation process in accordance with this invention.

The yield or recovery of the desired purified cell population can be increased by using a counter-current processing technique in which multiple stage positive selection is combined with multiple stage depletion. FIG. 4 is a schematic representation of a counter-current multiple stage positive selection method for the purification of cells. Blocks 40, 42, 44, 46, and 48 are affinity cell separation devices with affinity contact surfaces 50, both devices and surfaces being of the types described above. The cell separation devices for batch types may each be the same or differ in type and there may be two or more total devices in number. In FIG. 4, five devices are illustrated.

The affinity surfaces are coated with a ligand, of the type described above, which binds the cell population to be purified with a specific affinity. In a batch type operation, the operation of the several devices 40 to 48, inclusive, is similar to that previously described. The positively selected cells removed from the affinity surfaces 50 are each moved down the chain, as represented by the lines 52, to a different contacting surface 50 in one of the devices 40 to 48, inclusive. In each case, the selected or desired cells are placed into a fresh media for contact with the new surface 50. After each use, the particular device 40 to 48, inclusive, may be removed and replaced by a fresh device or more preferably a fresh affinity surface is positioned within the device.

Conversely, the unbound cells that are removed with the media from the respective devices 40 to 48, inclusive, travel upwardly in the schematic of FIG. 4, as represented by the lines 54. A wash solution 56 is introduced into the lower device 48. Purified cells are removed from device 48. The depleted cell mixture is removed from the upper device 40 through the line 58. Cells to be separated are introduced into the middle device 44 as represented by line 60.

Thus in an illustrative application of the batch method, cells to be separated are passed in a mixture into the device 44. After contact with the affinity surface 50 within the device 44, the unbound cells are removed by the media from the wash line 54 and introduced into device 42 for contact with its affinity surface 50. The bound cells are removed from the affinity surface 50 within device 44, resuspended in media and applied to device 46 for contact with its affinity surface 50. Next the unbound cells from device 42 are applied via stream 54 to device 40 for contact with its affinity surface 50 and the bound cells are resuspended and applied to device 44 for contact with its affinity surface 50. The unbound cells from device 40 pass through the outlet and constitute the depleted cell mixture, while the cells bound in device 40 are resuspended in media and applied to device 42 for contact with its affinity surface 50. Depending on the yield required, the bound cells in device 42 are resuspended and applied to device 44, thence to device 46 and so on.

In the meantime, cells not bound to the surface 50 in device 46 are removed by wash line 54 and introduced into the device 44 for contact with its affinity surface 50. Conversely, bound cells are removed from the affinity surface 50 of device 46, resuspended in media and applied to device 48 for contact with its affinity surface 50. The unbound cells in device 48 are applied via stream 54 to device 46 for contact with its affinity surface 50. The bound cells in device 48 are removed from the affinity surface 50 in device 48 and passed to the outlet 50 as highly purified cells and with a high yield as described. The several batch cycles may be continued to further increase cell yield as desired.

The counter-current batch operation requires repetitive operations at each of the stages. Following each application and removal of cells, a stage must be cleaned and resupplied with an appropriate contacting surface. The batch operation procedure described above provides highly pure desired cells as well as a high yield.

The same kind of counter-current method may be used in a continuous flow device such as a vertically oriented column 90 of suitable material such as glass as seen in FIG. 5, with media entering near the bottom at an inlet 92 and leaving near the top through an outlet 94. Cell mixtures are introduced into the column through an inlet 102 between the media entrance and exit ports. Appropriate surfaces, coated with affinity ligand, such as provided by particles denser than the media or cells, are introduced at the top of the column as at 96 and allowed to settle slowly down through the column 90 to contact the cells rising with the media. Cells which bind to the particles will be pulled down through the column until they desorb from the particles. Nonspecifically bound cells desorb faster than cells bound specifically by affinity ligand. Cells which are bound to particles long enough will be carried out of the bottom of the column through a valve 98 and exit outlet 100. If the particles settle slowly enough to remain in the column while specifically bound cells to bind, desorb, and bind again more than once (an hour or more) then this device will be an effective multistage counter-current cell separation device. The media and particles must be selected accordingly. If bouyant particles are used, the media flow direction must be switched and the particles introduced at the bottom of the column.

In still another alternative, a batch type process such as depicted in FIG. 6 may be employed. In this schematic, a plurality of affinity surfaces, which may be any of the types described hereinbefore are depicted by the reference numerals 80, 82, 84, 86 and 88. Each affinity surface represents a stage which would be some type of a receptacle or container for holding the media associated with that particular stage. The surfaces are grouped in stages or clusters of two and three surfaces to accommodate appropriate interchange therebetween. Cell mixtures are introduced, as denoted by the arrow at 81, to the first stage 80. After contact with the affinity surface 80 of the first stage, the unbound cells, depicted by the numeral 1N, are transferred and introduced into the upper surface 82 of the second stage. The bound cells are removed from the affinity surface 80 and transferred, as depicted by the line 1A, to the lower affinity surface 82 of the second stage. Unbound cells from the upper stage 82 are passed to the third stage upper affinity surface 84. Bound cells are removed from the upper surface 82 and passed, as depicted by the line 2A, to the middle affinity surface 84. Likewise unbound cells from the lower affinity surface 82 are passed, as denoted by the line 3N, to the mid-affinity surface 84. Finally bound cells are removed from the lower surface 82 and passed onto the lower affinity surface 84 as noted by the arrow 3A.

Unbound cells from the upper third stage affinity surface 84 are passed, as denoted by the line 4N, to waste. Bound cells from the same stage are removed, as denoted by the line 4A, and introduced to the upper affinity surface 86 of the fourth stage. Similarly the unbound cells from the middle third stage surface 84 are passed, as denoted by the line 5N, to the upper fourth stage affinity surface 86. Bound cells are removed from the middle affinity surface 84 and passed, as denoted by the line 5A, to the lower fourth stage affinity surface 86. To complete the cycle, unbound cells from the lower third stage affinity surface 84 are passed to the lower fourth stage affinity surface 86 via the line 6N whereas bound cells on the lower third stage affinity surface 84 are passed as denoted by the line 6A to a collection device where the high purity desired cells are collected. This sequence repeats itself to achieve the desired yields. Thus unbound cells from surfaces 86 are passed via lines 7N or 8N to appropriate surfaces 88 of a further stage as shown. Bound cells are passed via lines 7A or 8A to surfaces 88 of this further stage as shown. The fifth stage lower surface 88 provides high purity cells as denoted by line 11A; conversely, the line 9N passes to waste media depleted of the desired cells.

EXAMPLE 1

Attachment of Antibodies to a Culture Dish Surface

The following procedure was used to bind antibodies to the surface of a culture dish. Goat anti-rat IgM antibody was immobilized on polystyrene tissue culture dishes at a concentration of 0.1 µg/cm$^2$ using the following procedure.

A volume of 0.3 ml of a carbodiimide solution (0.05 g of carbodiimide hydrochloride per ml of 0.1M sodium acetate pH 4.8) and 0.3 ml containing 0.96 µg goat anti-rat IgM per ml of 0.1M sodium acetate pH 4.8 were added to each 35 mm culture dish well. The dish was incubated with rocking for 60 minutes at 25° C. The wells were washed 3 times with 3 ml of PBS. A second or capture antibody was added in 3 ml of PBS at a concentration of 3 µg/ml to each dish. The dish was again incubated at room temperature for 1 hour without mixing. Excess antibody was rinsed off with two 3 ml aliquots of PBS and one aliquot of PBS containing 1% heat inactivated fetal calf serum (FCS) (Gibco). The remaining protein binding sites on the plate were blocked or quenched by adding 0.1% bovine serum albumin (BSA) in 3 ml of PBS to the dish. The dish was then incubated for 30 minutes at room temperature without mixing. The dish was finally rinsed 3 times with aliquots of 3 ml PBS. In one case the second antibody was that designated 187.1, was specific to mouse immunoglobulin, and was obtained from John McKearn (E. I. du Pont de Nemours and Company, Glenolden, Pa.). In another case it was the mouse immunoglobulin designated 7D4.

EXAMPLE 2

Multiple Stage Planning

An example of affinity cell selection by multiple stage panning is detailed below. Mouse CTLL cells (American Type Culture Collection #PlB-214), which are in this case the target cell to be purified, were mixed with human HUT-102 cells (American Type Culture Collection #PlB-162) at a resultant concentration of 10% target CTLL cells. Polystyrene tissue culture dishes were coated with an IgM monoclonal antibody (mAb) specific for the IL2 receptor present on the surface of the CTLL cells. The mAb is designated 7D4 and was obtained from Tom Waldmann, NCI, Bethesda, Md. The antibody was attached to the polystyrene surface using the procedure given in Example 1.

The CTLL and HUT cells were collected by centrifugation in at 15 ml centrifuge tube for 10 minutes at 1000xg. The media was decanted and the cells were then resuspended in Iscove's medium (Gibco) containing 15% fetal bovine serum (FBS). The suspended cells were then poured into the mAb 7D4-containing petri dish, and incubated at 22° C. for one hour. The nonadherent cells were removed by rinsing the petri dish surface with PBS. The adherent cells were scraped off the petri dish surface with a PVC scraper and resuspended in Iscove's medium containing 15% FBS. The resuspended adherent cells were then poured into a fresh petri dish similarly coated with the same anti-IL2 receptor mAb (7D4). Following washing to remove the nonadherent cells, the adherent cells were again removed by scraping. The scraped cells were resuspended and captured in a third anti-IL2 receptor mAb 7D4- containing petri dish. Again the nonadherent cells were removed by rinsing.

The adherent cells were removed by scraping, resuspended and analyzed both by flow cytometry and by limiting dilution assay. Flow cytometry showed that greater than 99% of the adherent cells were CTLL cells while the limiting dilution assay showed a ratio of HUT to CTLL cells of 1:200 (99.5% CTLL cells). The limiting dilution assay was carried out by diluting the adherent cells to various numbers per well in a 96-well plate containing IL2-free media. Under such conditions the contaminating HUT cells are able to grow, whereas the CTLL target cells, which require IL2 for growth, are unable to grow (Gillis and Smith, 1977, *Nature* 268:154–156). Growth was seen in half the wells initially containing 100 cells. Thus, the limiting dilution assay showed approximately 0.5 HUT cells per 100 total cells (HUT plus CTLL). Thus, the three-stage affinity cell selection or panning procedure resulted in the target CTLL cells being concentrated from 10% to 99.5%. The yield from this three-stage panning procedure was 14%.

EXAMPLE 3

Affinity Selection of Surface Immunoglobulin-bearing Spleen Cells from Mouse Spleen Homogenates Cells were obtained from the spleen from BALB/c mice. The cells were suspended by scrubbing the spleen against a stainless steel screen and rinsing the screen with PBS. Clumps of cells were removed by filtering the suspension through cotton. The cells were washed and resuspended in cold Iscove's medium with 15% FCS at a concentration of 10$^6$ cells/ml.

In the first stage of the separation, the cells were added to dishes containing immobilized antibody as described above in Example 1 at 2×10$^5$ cells/cm$^2$ and incubated at 4° C. for 1 hour. The nonadherent cells were rinsed away using 8 aliquots of 3 ml PBS containing 1% FCS. The adherent cells were scraped and resuspended in cold Iscove's medium containing 15% FCS. In the second stage of the separation the removed cells were added to fresh dishes at 3×10$^5$ cells/cm$^2$ for 1 hour at 4° C. The nonadherent cells were rinsed away as above and the adherent cells were Scraped and resuspended in Iscove's containing 15% FCS.

The purity of the resultant cells were assayed by staining the purified cells with fluorescein-labeled 187.1 mAb and measuring the fluorescence using an Ortho Spectrum flow cytometer. The starting mixture was 39% 187.1 positive while the purified cells were over 99% 187.1 positive.

EXAMPLE 4

Purification of CTLL Cells From Contaminating Bacteria

In an unusual application, bacteria-free cells were isolated from a cell culture contaminated with bacteria. In one experiment, 5×10$^8$ ml *Bacillus pumilus* were added to a 10$^6$/ml CTLL culture at room temperature. The CTLL cells were isolated using three stages of positive cell selection on culture plates coated with mAb 7D4. The mAb 7D4 was attached to the culture plate as described in Example 1. The three-stage positive selection procedure was performed as described in Example 2. The adherent cells obtained following the three-stage positive selection procedure were analyzed for the presence of contaminating bacteria using a limiting dilution assay. The adherent cells were diluted into wells and cultured. The affinity-purified CTLL cells diluted up to 100 per well grew normally and were bacteria free. The initial concentration of CTLL cells of 0.2% were thereby increased to at least 98.8% by the process. This is a new method for preparing bacteria-free cultures of mammalian cells.

EXAMPLE 5

Multiple Stage Particle Technique

The magnetic particles used by Gaudernack et al. (op. cit.) are useful for affinity cell separations. By using multiple stages, however, their performance was greatly improved.

Magnetic polystyrene particles of 4.5 micron diameter (Dynal M-450) were coated with mAb 7D4, which is specific for the mouse IL2 receptor, using the following procedure $10^7$ magnetic particles and 1.0 µg/cm$^2$ mAb 7D4 were added to 1 ml PBS, where the area (cm$^2$) is the calculated surface area of the magnetic beads assuming they are solid spheres. The mixture was incubated for 2 hours 25° C. and mixed frequently. The magnetic particles were washed 2 times with aliquots of 1 ml PBS by retaining the particles with a magnet. 2 mg/cm$^2$ of BSA in 1 ml PBS was added to the magnetic particles. The sample was mixed to resuspend particles and then incubated 30 minutes 25° C. The magnetic particles were washed 2 times with aliquots of 1 ml PBS by retaining the particles with a magnet. The particles were suspended in Iscove's media containing 15% FBS at a concentration of $10^7$ particles/ml.

A mixture of 10% CTLL cells (the target cell to be purified) and 90% HUT-102 cells, at a concentration of $10^6$/ml and $10^7$/ml, respectively, was added to the 7D4-coated magnetic particles and incubated for 20 minutes at room temperature. The nonadherent cells were washed away by retaining the particles and attached cells with a magnet.

The adherent cells were removed from the particles by natural desorption over a two hour period at room temperature. The desorbed cells were collected and resuspended with fresh mAb-coated particles for 20 minutes at room temperature.

The purified adherent cells were analyzed by limiting dilution and flow cytometry. Flow cytometry showed greater than 99% CTLL cells while the limiting dilution assay showed greater than 99.97% purity of CTLL cells.

EXAMPLE 6

Counter-Current Process

The multistage process described above in Example 5 gives excellent purity at the expense of yield. By combining multistage positive selection with multistage depletion, high purity and high yield can both be achieved. 10% CTLL cells were mixed with 90% HUT-102 cells, at a resultant concentration of $10^6$/ml and $10^7$/ml, respectively, in Iscove's medium containing 15% FBS. The mixture was poured into a petri dish, with appropriate mAb capture reagent on the dish bottom, as described in Example 1, and incubated for 1 hour at room temperature. The nonadherent cells were resuspended in media and poured into a fresh mAb-coated dish. The adherent cells from both dishes were scraped, resuspended, and then poured into a third mAb-coated dish. The final adherent cells were removed and analyzed by flow cytometry and limiting dilution assay. The first dish adherents were 58% CTLL cells with a yield of 50%; the nonadherents of the first dish were 2% CTLL with a yield of approximately 50%. The adherents from the second dish were 15% CTLL cells with a yield of 60%. The adherents from the third dish were 80% CTLL cells with an overall yield of 40%. A corresponding two-stage process without the counter-current treatment gave 86% purity of CTLL cells with 25% yield.

What is claimed is:

1. An affinity method of providing high purity fractions of desired cells by separating the desired cells from a mixture of cells using plural surfaces having ligands, with a high affinity for the desired cells, immobilized thereon comprising the steps of:

(a) contacting one of the surfaces with the mixture of cells suspended in a first media to permit some of the desired cells to be bound to the one surface;

(b) separating unbound cells and the first media from bound cells;

(c) removing the bound cells from the one surface, and resuspending said bound cells in a second media;

(d) contacting a different one of the surfaces with the second media containing said resuspended cells to permit some of the removed cells of step (c) to be bound thereto;

(e) separating the unbound cells and the second media from the different surface; and (f) removing the bound cells of step (d) from the different surface to provide the high purity fraction of desired cells.

2. The method as set forth in claim 1 which includes the additional steps of resuspending the removed cells of step (f) in a third media and repeating steps (d) and (e) with a third one of the surfaces with the removed cells of step (f).

3. The method as set forth in claim 2 wherein the surfaces each comprise the bottom of a different container.

4. The method as set forth in claim 2 wherein the surfaces comprise the interior wall of roller bottles.

5. The method as set forth in claim 1 wherein the surfaces each comprise the bottom of a different container.

6. The method as set forth in claim 1 wherein the surfaces comprise the surfaces of magnetic particles.

7. The method of claim 6 wherein the unbound cells and media are separated from the bound cells by separating the magnetic particles therefrom, desorbing the bound cells from the magnetic particles, and resuspending the desorbed cells together with fresh ligand immobilized magnetic particles in a different media.

8. The method as set forth in claim 1 wherein the surfaces comprise the interior wall of roller bottles.

9. The method as set fort in claim 1 wherein each of the surfaces has a different ligand, each ligand having a different affinity for the desired cells immobilized thereon.

10. The method as set forth in claim 1 wherein steps (a) through (f) result in at least a 2.9-fold enrichment of the bound cells.

11. The method of claim 1 wherein the surfaces comprise affinity coated surfaces.

* * * * *